United States Patent
Goget et al.

(10) Patent No.: US 8,092,552 B2
(45) Date of Patent: Jan. 10, 2012

(54) DYEING COMPOSITION COMPRISING AMMONIUM CHLORIDE, METHOD OF COLOURING KERATIN FIBERS, AND DEVICE

(75) Inventors: Caroline Goget, Paris (FR); François Cottard, Courbevoie (FR); Florence Laurent, Bois Colombes (FR); Jean-Marc Ascione, Paris (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 12/412,666

(22) Filed: Mar. 27, 2009

(65) Prior Publication Data

US 2009/0282623 A1 Nov. 19, 2009

Related U.S. Application Data

(60) Provisional application No. 61/071,012, filed on Apr. 9, 2008, provisional application No. 61/071,013, filed on Apr. 9, 2008.

(30) Foreign Application Priority Data

Mar. 28, 2008 (FR) ...................................... 08 52063
Mar. 28, 2008 (FR) ...................................... 08 52064

(51) Int. Cl.
*A61Q 5/10* (2006.01)
(52) U.S. Cl. ............. 8/405; 8/406; 8/435; 8/552; 8/554; 8/619; 8/620
(58) Field of Classification Search ............. 8/405, 406, 8/435, 552, 554, 619, 620
See application file for complete search history.

(56) References Cited

U.S. PATENT DOCUMENTS

| 5,334,225 | A * | 8/1994 | Ogawa et al. ..................... 8/408 |
| 2002/0088063 | A1 | 7/2002 | Ohashi et al. |
| 2003/0172472 | A1 * | 9/2003 | Laurent ............................. 8/405 |
| 2003/0208856 | A1 | 11/2003 | Miyabe et al. |
| 2006/0032002 | A1 * | 2/2006 | Bolton et al. .................... 8/405 |
| 2006/0272106 | A1 | 12/2006 | Nöcker et al. |
| 2007/0136959 | A1 | 6/2007 | Fadli |
| 2007/0157399 | A1 | 7/2007 | Nobuto et al. |

FOREIGN PATENT DOCUMENTS

| DE | 197 35 852 A1 | 2/1999 |
| EP | 1 155 679 A2 | 11/2001 |
| EP | 1 832 276 A1 | 9/2007 |
| JP | 01165514 | 6/1989 |
| WO | WO 2009/050295 | 4/2009 |

OTHER PUBLICATIONS

French Search Report for FR 0852063, dated Nov. 13, 2008.
French Search Report for FR 0852064, dated Nov. 14, 2008.
English language abstract of DE 197 35 852, Feb. 15, 1999.
European Search Report for EP 2 111 842 A1, dated Jul. 1, 2009.

* cited by examiner

*Primary Examiner* — Eisa Elhilo
(74) *Attorney, Agent, or Firm* — Finnegan, Henderson, Farabow, Garrett & Dunner, LLP

(57) ABSTRACT

The present invention provides a dyeing composition comprising, in a cosmetically acceptable medium, one or more oxidation dyes, aqueous ammonia, ammonium chloride and one or more additives selected from ceramides, silicas, ascorbic acid and/or its salts, fatty acids and/or salts thereof, alkanolamines and/or salts thereof, crosslinked homopolymers of acrylic acid, copolymers of dialkyldiallylammonium chloride and acrylic acid, and particular cationic polymers, or mixtures thereof. It likewise provides a method of colouring human keratin fibres, employing the said composition in the presence of a composition comprising one or more oxidizing agents. The invention further provides a multiple-compartment device appropriate to the implementation of the said method, comprising in a first compartment a dyeing composition according to the invention and in another compartment a composition comprising one or more oxidizing agents.

11 Claims, No Drawings

DYEING COMPOSITION COMPRISING AMMONIUM CHLORIDE, METHOD OF COLOURING KERATIN FIBERS, AND DEVICE

CROSS-REFERENCE TO RELATED APPLICATIONS

This application claims benefit of priority under 35 U.S.C. §119 to French Patent Application No. 0852063, filed Mar. 28, 2008, and to French Patent Application No. 0852064, filed Mar. 28, 2008, and the benefit of U.S. Provisional Application No. 61/071,012, filed Apr. 9, 2008, and U.S. Provisional Application No. 61/071,013, filed Apr. 9, 2008, the content of all of which is incorporated herein by reference.

The present invention relates to a composition comprising, in a cosmetically acceptable medium, one or more oxidation dyes, aqueous ammonia, ammonium chloride and at least one particular additive. It also pertains to a method of colouring human keratin fibres, employing the said composition, and to a multiple-compartment device appropriate for the implementation of the said method.

The processes of colouring human keratin fibres, such as the hair, include permanent or oxidation dyeing. This mode of colouring makes use more particularly of one or more oxidation dyes, more particularly one or more oxidation bases optionally in combination with one or more couplers.

Typically the oxidation bases are selected from ortho- or para-phenylenediamines, ortho- or para-aminophenols and heterocyclic compounds. These oxidation bases are colourless or lightly coloured compounds which, in combination with oxidizing products, allow coloured species to be obtained, by a process of oxidative condensation.

The shades obtained with these oxidation bases are very often varied by combining them with one or more couplers, the latter being selected in particular from aromatic meta-diamines, meta-aminophenols, meta-diphenols and certain heterocyclic compounds, such as indole compounds.

The variety of the molecules employed for the oxidation bases and couplers allows a rich palette of colours to be obtained.

The method of colouring involves contacting the oxidation dye or dyes with an oxidizing agent, which is preferably hydrogen peroxide, under alkaline conditions.

During the application time of the dyeing composition in the presence of the oxidizing agent, two phenomena occur. One of them involves a lightening of the keratin fibres through the combined action of the alkaline agent and the oxidizing agent; the other involves the oxidative condensation reaction which occurs after the dyes have spread to the interior of the fibre, and which leads to the coloured species.

Traditionally the application time is of the order of around thirty minutes, although the current tendency is to consider such a period to be too long.

In order to solve this problem it is not reasonably possible to consider simply reducing the application time of the conventional compositions. Indeed, it is clear that it would be difficult to maintain the same level of efficacy of such compositions, and in particular to maintain satisfactory levels of lightening and of colouring, if they were to be employed under these shortened-period conditions.

Furthermore, it would be possible to consider increasing the power of the oxidizing agent and the alkaline agent, by employing, for example, oxidizing agents of the type of the persalts, and/or alternatively by increasing the pH of the composition applied. However, such an option is relatively undesirable, in the sense that the means employed would increase the risk of degradation of the keratin fibre.

There is therefore a real need to be able to have dyeing compositions available, employing oxidation dyes, that allow the degradation of the treated keratin fibres to be limited, while retaining, or even improving, the levels of colouring and of lightening in relation to those obtained with the conventional methods, within application times which may be, advantageously, of the order of 20 minutes at most, and more particularly of around fifteen minutes.

These objectives, and others, are achieved by the present invention, which provides a composition for colouring human keratin fibres, comprising, in a cosmetically acceptable medium, one or more oxidation dyes, aqueous ammonia, and ammonium chloride and one or more additives selected from ceramides, silicas, ascorbic acid and/or its salts, fatty acids and/or salts thereof, alkanolamines and/or salts thereof, crosslinked homopolymers of acrylic acid, copolymers of dialkyldiallylammonium chloride and acrylic acid, cationic polymers composed of repeat units of formula A below:

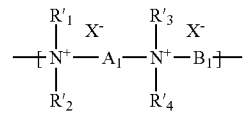

in which $R'_1$, $R'_2$, $R'_3$ and $R'_4$, which are identical or different, represent aliphatic, alicyclic or aryl aliphatic groups containing 1 to 6 carbon atoms, or aliphatic hydroxy($C_1$-$C_6$)alkyl groups, or else $R'_1$, $R'_2$, $R'_3$ and $R'_4$, together or separately, constitute, with the nitrogen atoms to which they are attached, saturated heterocycles having five or six members, optionally comprising a second heteroatom other than nitrogen (for example oxygen or sulphur), or else $R'_1$, $R'_2$, $R'_3$ and $R'_4$ represent a linear or branched $C_1$-$C_6$ alkyl group substituted by a nitrile, ester, acyl, amide or —CO—O—$R'_5$-D or —CO—NH—$R'_5$-D group where $R'_5$ iS a $C_1$-$C_6$ alkylene group and D is a quaternary ammonium group containing $C_1$-$C_6$ alkyl groups which are identical or not;

$A_1$ and $B_1$ represent polymethylene groups containing 2 to 6 carbon atoms, which may be linear or branched, saturated or unsaturated, and may contain, bonded to (substituent) or intercalated in the main chain, a $C_6$ aromatic ring, or an oxygen or sulphur atom, or sulphoxide, sulphone, disulphide, amino, alkylamino, hydroxyl, quaternary ammonium, ureido or ester groups, or combinations thereof, and $X^-$ denotes an anion derived from an organic or inorganic acid;

$A_1$, $R'_1$, and $R'_3$ may form, with the two nitrogen atoms to which they are attached, a piperazine ring, and mixtures of these additives.

The invention also provides a method of colouring human keratin fibres, in which the dyeing composition described above is applied in the presence of an oxidizing agent.

The invention lastly provides a multiple-compartment device comprising in a first compartment a composition as defined above, without oxidizing agent, and in another compartment a composition comprising one or more oxidizing agents.

It has in fact been noticed that the composition according to the invention allowed improvements in the power, the rise and the homogeneity of the colouring obtained, even with application times for the composition of the order of twenty minutes at most.

Other features and advantages of the invention will become more clearly apparent on reading the description and examples.

It should be noted that, in the text below, in the absence of any indication to the contrary, the end points of a range of values are included in that range.

Moreover, the human keratin fibres treated by the method according to the invention are preferably the hair.

As indicated above, the composition according to the invention comprises ammonium chloride.

Preferably the ammonium chloride is present in the composition in an amount of more than 1% by weight, relative to the weight of the composition.

According to one more particular embodiment of the invention the amount of ammonium chloride is at least 1.5% by weight and preferably at least 3% by weight, relative to the weight of the composition.

Advantageously the amount of ammonium chloride represents between 1% and 15% by weight, more particularly between 1.5% and 10% by weight and preferably between 3% and 7% by weight relative to the composition weight, The dyeing composition according to the invention further comprises aqueous ammonia.

More particularly the amount of aqueous ammonia in the composition, expressed in terms of gaseous ammonia, is at least 0.5% by weight, relative to the weight of the composition.

According to one advantageous variant of the invention the amount of aqueous ammonia, expressed in terms of gaseous ammonia, is between 0.5% and 4% by weight, more particularly between 0.7% and 2.5% by weight and preferably between 1% and 2% by weight, relative to the weight of the composition.

In accordance with one preferred embodiment of the invention the respective amounts of ammonium chloride and of aqueous ammonia in the composition are such that the ammonium chloride/aqueous ammonia (expressed in terms of gaseous ammonia) weight ratio is at least 2. According to an even more preferred variant the weight ratio is between 2 and 10, better still between 2.3 and 8, and preferably between 2.5 and 5.

The composition according to the invention further comprises one or more oxidation dyes. More particularly the oxidation dye or dyes correspond to one or more oxidation bases, optionally in combination with one or more couplers.

As examples of oxidation bases, the latter are selected from para-phenylenediamines, bisphenyl-alkylenediamines, para-aminophenols, ortho-amino-phenols, heterocyclic bases and their addition salts.

The para-phenylenediamines include for example para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N—N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl) amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N—N-dimethyl-3-methyl-para-phenylenediamine, N—N-(ethyl, β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene, 3-hydroxy-1-(4'-aminophenyl)pyrrolidine and their addition salts with an acid.

Among the para-phenylenediamines cited above, para-phenylenediamine, para-tolylenediamine, 2-iso-propyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, 2-β-acetylaminoethyloxy-para-phenylenediamine, and their addition salts with an acid, are particularly preferred.

The bisphenylalkylenediamines include for example N,N'-bis(β-hydroxyethyl)-N—N'-bis(4'-aminophenyl)-1,3-diaminopropanol, N,N'-bis(β-hydroxyethyl)-N,N'-bis(4'-aminophenyl)ethylenediamine, N/N'-bis(4-aminophenyl)-tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3-methylphenyl)ethylene-diamine, 1,8-bis(2,5-diaminophenoxy)-3,6-dioxaoctane), and their addition salts.

The para-aminophenols include for example para-aminophenol, 4-amino-3-methylphenol, 4-amino-3-fluoro-phenol, 4-amino-3-chlorophenol, 4-amino-3-hydroxy-methylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethyl-aminomethyl)phenol, 4-amino-2-fluorophenol, and their addition salts with an acid.

The ortho-aminophenols include for example 2-aminophenol, 2-amino-5-methylphenol, 2-amino-6-methyl-phenol, 5-acetamido-2-aminophenol, and their addition salts.

The heterocyclic bases include for example pyridine derivatives, pyrimidine derivatives and pyrazole derivatives.

The pyridine derivatives include the compounds described for example in patents GB 1 026 978 and GB 1 153 196, such as 2,5-diaminopyridine, 2-(4-methoxyphenyl)amino-3-aminopyridine and 3,4-diamino-pyridine, and their addition salts.

Other pyridine oxidation bases useful in the present invention are the 3-aminopyrazolo[1,5-a]pyridine oxidation bases or their addition salts that are described for example in patent application FR 2801308. Examples include pyrazolo[1,5-a]pyridin-3-ylamine; 2-acetylaminopyrazolo[1,5-a]pyridin-3-ylamine; 2-morpholin-4-ylpyrazolo[1,5-a]pyridin-3-ylamine; 3-aminopyrazolo[1,5-a]pyridine-2-carboxylic acid; 2-methoxypyrazolo[1,5-a]pyridin-3-ylamine; (3-aminopyrazolo[1,5-a]pyridin-7-yl)methanol; 2-(3-aminopyrazolo[1,5-a]pyridin-5-yl)ethanol; 2-(3-aminopyrazolo[1,5-a]pyridin-7-yl)ethanol; (3-aminopyrazolo[1,5-a]-pyridin-2-yl)methanol; 3,6-diaminopyrazolo[1,5-a]-pyridine; 3,4-diaminopyrazolo[1,5-a]pyridine; pyrazolo[1,5-a]pyridine-3,7-diamine; 7-morpholin-4-ylpyrazolo[1,5-a]pyridin-3-ylamine; pyrazolo[1,5-a]pyridine-3,5-diamine; 5-morpholin-4-ylpyrazolo[1,5-a]pyridin-3-ylamine; 2-[(3-aminopyrazolo[1,5-a]pyridin-5-yl)-(2-hydroxyethyl)amino] ethanol; 2-[(3-aminopyrazolo[1,5-a]pyridin-7-yl)-(2-hydroxyethyl)amino]ethanol; 3-amino-pyrazolo[1,5-a]pyridin-5-ol; 3-aminopyrazolo[1,5-a]-pyridin-4-ol; 3-aminopyrazolo[1,5-a]pyridin-6-ol; 3-aminopyrazolo[1,5-a]pyridin-7-ol; and their addition salts.

The pyrimidine derivatives include the compounds described for example in patents DE 2359399, JP 88-169571, JP 05-63124 and EP 0770375 or patent application WO 96/15765, such as 2,4,5,6-tetra-aminopyrimidine, 4-hydroxy-2,5,6-triaminopyrimidine, 2-hydroxy-4,5,6-triaminopyrimidine, 2,4-dihydroxy-5,6-di-aminopyrimidine, 2,5,6-triaminopyrimidine and their addition salts and their tautomeric forms, when a tautomeric equilibrium exists.

The pyrazole compounds include the compounds described in patents DE 3843892 and DE 4133957 and patent applications WO 94/08969, WO 94/08970, FR-A-2 733 749 and DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)-pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'methoxyphenyl)pyrazole, 4,5-diamino-1-ethyl-3-hydroxymethyl-pyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triamino-pyrazole, 1-methyl-3,4,5-triaminopyrazole, 3,5-diamino-1-methyl-4-methylaminopyrazole, 3,5-diamino-4-(β-hydroxyethyl)amino-1-methylpyrazole, and their addition salts. It is also possible to use 4,5-diamino-1-(β-methoxyethyl)pyrazole.

Further pyrazole derivatives include the diamino-N,N-dihydropyrazolopyrazolones and in particular those described in application FR 2886136 such as the following compounds and their addition salts: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]-pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]-pyrazol-1-one, 4,5-diamino-1,2-dimethyl-1,2-dihydro-pyrazol-3-one, 4,5-diamino-1,2-diethyl-1,2-dihydro-pyrazol-3-one, 4,5-diamino-1,2-di(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-di-hydropyrazol-3-one, 2,3-diamino-6-hydroxy-6,7-dihydro-1H,5H-pyrazolo[1,2-a]pyrazol-1-one.

As heterocyclic bases it will be preferred to use 4,5-diamino-1-(β-hydroxyethyl)pyrazole and/or 2,3-diamino-6,7-dihydro-1H,5H-pyrazolo[1,2-a]pyrazol-1-one and their addition salts.

With regard to the couplers, mention may be made in particular of meta-phenylenediamines, meta-aminophenols, meta-diphenols, naphthalenic couplers, heterocyclic couplers and their addition salts.

Examples include 1,3-dihydroxybenzene, 1,3-dihydroxy-2-methylbenzene, 4-chloro-1,3-dihydroxy-benzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxy-benzene, α-naphthol, 2-methyl-1-naphthol, 6-hydroxy-indole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)-amino-3,4-methylenedioxybenzene, 2,6-bis(β-hydroxyethylamino)toluene, 6-hydroxyindoline, 2,6-dihydroxy-4-methylpyridine, 1H-3-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole, 6-methyl-pyrazolo[1,5-a]benzimidazole, their addition salts with an acid, and mixtures thereof.

Generally speaking, the addition salts of the oxidation bases and of the couplers that can be used in the context of the invention are selected in particular from addition salts with an acid, such as hydrochlorides, hydrobromides, sulphates, citrates, succinates, tartrates, lactates, tosylates, benzenesulphonates, phosphates and acetates.

The oxidation base or bases represent advantageously from 0.0001% to 10% by weight, relative to the weight of the composition, and preferably from 0.005% to 5% by weight, relative to the weight of the composition.

The amount of coupler or couplers, when present, represent advantageously from 0.0001% to 10% by weight, relative to the weight of the composition, and preferably from 0.005% to 5% by weight, relative to the weight of the composition.

As indicated above, the composition according to the invention comprises one or more additives selected from ceramides, silicas, ascorbic acid and/or its salts, fatty acids and/or salts thereof, alkanolamines and/or their salts, crosslinked homopolymers of acrylic acid, copolymers of dialkyldiallylammonium chloride and acrylic acid, cationic polymers composed of repeat units of formula A below:

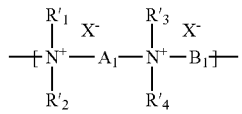

in which $R'_1$, $R'_2$, $R'_3$ and $R'_4$, which are identical or different, represent aliphatic, alicyclic or aryl aliphatic groups containing 1 to 6 carbon atoms, or aliphatic hydroxy($C_1$-$C_6$)alkyl groups, or else $R'_1$, $R'_2$, $R'_3$ and $R'_4$, together or separately, constitute, with the nitrogen atoms to which they are attached, saturated heterocycles having five or six members, optionally comprising a second heteroatom other than nitrogen (for example oxygen or sulphur), or else $R'_1$, $R'_2$, $R'_3$ and $R'_4$ represent a linear or branched $C_1$-$C_6$ alkyl group substituted by a nitrile, ester, acyl, amide or —CO—O—$R'_5$-D or —CO—NH—$R'_5$-D group where $R'_5$ is a $C_1$-$C_6$ alkylene group and D is a quaternary ammonium group containing $C_1$-$C_8$ alkyl groups which are identical or not;

$A_1$ and $B_1$ represent polymethylene groups containing 2 to 6 carbon atoms, which may be linear or branched, saturated or unsaturated, and may contain, bonded to (substituent) or intercalated in the main chain, a $C_6$ aromatic ring, or an oxygen or sulphur atom, or sulphoxide, sulphone, disulphide, amino, alkylamino, hydroxyl, quaternary ammonium, ureido or ester groups, or combinations thereof, and $X^-$ denotes an anion derived from an organic or inorganic acid;

$A_1$, $R'_1$ and $R'_3$ may form, with the two nitrogen atoms to which they are attached, a piperazine ring; and mixtures of these additives.

The amount of each of the aforementioned additives represents more particularly from 0.01% to 10% by weight, preferably from 0.005% to 5% by weight, relative to the weight of the composition.

The term "ceramide" refers in particular to compounds corresponding to the formula (B) below:

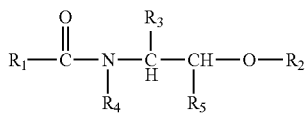

in which:

$R_1$ denotes:
  alternatively a saturated or unsaturated, linear or branched $C_1$-$C_{50}$, preferably $C_5$-$C_{50}$, hydrocarbon radical, it being possible for this radical to be substituted by one or more, and preferably one to six, hydroxyl groups which are optionally esterified by an acid $R_7$COOH, $R_7$ being a linear or branched, saturated or unsaturated $C_1$-$C_{35}$ hydrocarbon radical which is optionally mono- or polyhydroxylated, with preferably from one to six hydroxyl groups, it being possible for the hydroxyl or hydroxyls of the radical $R_7$ to be esterified by a linear or branched, saturated or unsaturated $C_1$-$C_{35}$ fatty acid which is optionally mono- or polyhydroxylated with preferably from one to six hydroxyl groups,
  or a radical R"—(NR—CO)—R', where R denotes a hydrogen atom or a saturated or unsaturated, linear or branched $C_1$-$C_{20}$ hydrocarbon radical which is mono- or polyhydroxylated with preferably from one to six hydroxyl groups (preferably monohydroxylated), R' and R" are saturated or unsaturated, linear or branched hydrocarbon radicals, the sum of their carbon atoms being between 9 and 30, and R' being a divalent radical,
  or a radical $R_8$—O—CO—$(CH_2)_p$, where $R_8$ denotes a saturated or unsaturated, linear or branched $C_1$-$C_{20}$ hydrocarbon radical, and p is an integer ranging from 1 to 12;

$R_2$ is selected from a hydrogen atom, a saccharide radical, in particular a (glycosyl)$_n$, (galactosyl)$_m$ or sulphogalactosyl radical, a sulphate or phosphate residue, a phosphorylethylamine radical and a phosphorylethylammonium radical, in which n is an integer ranging from 1 to 4 and m is an integer ranging from 1 to 8;

$R_3$ denotes a hydrogen atom or a saturated or unsaturated, linear or branched $C_1$-$C_{33}$ hydrocarbon radical which is hydroxylated with preferably from one to six hydroxyl groups or is non-hydroxylated, it being possible for the hydroxyl or hydroxyls to be esterified by an inorganic acid or an acid $R_7$COOH, $R_7$ having the same meanings as above, it being possible for the hydroxyl or hydroxyls to be etherified by a (glycosyl)$_n$, (galactosyl)$_m$, suiphogalactosyl, phosphorylethylamine or phosphorylethylammonium radical, n is an integer ranging from 1 to 4 and m is an integer ranging from 1 to 8, it also being possible for $R_3$ to be substituted by one or more $C_1$-$C_{14}$ alkyl radicals;

$R_4$ denotes a hydrogen atom, a methyl or ethyl radical, a linear or branched, saturated or unsaturated $C_3$-$C_{50}$ hydrocarbon radical which is optionally hydroxylated, or a radical —$CH_2$—CHOH—$CH_2$—O—$R_6$ in which $R^6$ denotes a saturated or unsaturated, linear or branched $C_{10}$-$C_{26}$ hydrocarbon radical or a radical $R_8$—O—CO—$(CH_2)_p$, where $R_8$ denotes a saturated or unsaturated, linear or branched $C_1$-$C_{20}$ hydrocarbon radical and p is an integer ranging from 1 to 12, $R_5$ denotes a hydrogen atom or a linear or branched, saturated or unsaturated $C_1$-$C_{30}$ hydrocarbon radical which is optionally mono- or polyhydroxylated, with preferably from one to six hydroxyl groups, it being possible for the hydroxyl or hydroxyls to be etherified by a (glycosyl)$_n$, (galactosyl)$_m$, radical, where n represents an integer ranging from 1 to 4 and m represents an integer ranging from 1 to 8, or a sulphogalactosyl, phosphorylethylamine or phosphoryl-ethylammonium radical, with the proviso that, when $R_3$ and $R_5$ denote hydrogen or when $R_3$ denotes hydrogen and $R_5$ denotes methyl, $R_4$ does not denote a hydrogen atom or a methyl or ethyl radical.

The compounds of formula (B) above include very particularly the ceramides and/or glycoceramides that are described by Downing in Journal of Lipid Research, Vol. 35, page 2060, 1994, or those described in French patent application FR-2 673 179.

The preferred ceramides include those for which, in the formula (A), $R_1$ denotes an alkyl or alkenyl radical which is derived from $C_{14}$-$C_{22}$ fatty acids and is optionally hydroxylated; $R_2$ denotes a hydrogen atom; and $R_3$ denotes a saturated linear $C_{11}$-$C_{17}$ radical which is optionally hydroxylated, and preferably a $C_{13}$-$C_{15}$ radical.

Compounds of this type are selected, alone or in a mixture, from, for example, the following:
  N-linoleoyldihydrosphingosine,
  N-oleoyldihydrosphingosine or 2-oleamido-1,3-octa-decanediol,
  N-palmitoyldihydrosphingosine,
  N-stearoyldihydrosphingosine,
  N-behenoyldihydrosphingosine,
  N-2-hydroxypalmitoyldihydrosphingosine,
  N-stearoylphytosphingosine,
  N-palmitamidohexadecanediol.

It is also possible to use specific mixtures such as, for example, the mixtures of ceramide(s) 2 and of ceramide(s) 5 according to the Downing classification.

It is also possible to use the compounds of formula (B) for which $R_1$, denotes an alkyl or alkenyl radical derived from $C_{14}$-$C_{22}$ fatty acids; $R_2$ denotes a galactosyl or sulphogalactosyl radical; and $R_3$ denotes a saturated or unsaturated $C_{12}$-$C_{22}$ hydrocarbon radical and preferably a —CH=CH—$(CH_2)_{12}$—$CH_3$ group.

Ceramide compounds are described for example in patent applications DE 442-4530, DE 442-4533, DE 4402929, DE 4420736, WO 95/23807, WO 94/07844, EP 646572, WO 95/16665, FR 2673179, EP 227994 and WO 94/07844, WO 94/24097 and WO 94/10131, to which reference may be made.

Examples include the product composed of a mixture of glycoceramides that is sold under the trade name Glycocer® by Waitaki International Biosciences.

It is also possible to use the compounds described in patent applications EP 227994, EP 647617, EP 736522 and WO 94/07844.

Such compounds are, for example, Questamide H®, also called bis(N-hydroxyethyl-N-cetyl)malonamide and sold by Quest, and the N-(2-hydroxyethyl)-N-(3-cetyloxy-2-hydroxypropyl)amide of cetylic acid.

It is also possible to use N-docosanoyl-N-methyl-D-glucamine as described in international application WO 94/24097.

Preferably, if the composition comprises one or more ceramides, their amount represents from 0.001% to 1% by weight, preferably from 0.005% to 0.1% by weight, relative to the composition weight.

In accordance with one particularly advantageous variant of the invention, and when the composition comprises one or more ceramides, the ceramide(s)/ammonium chloride mass ratio is preferably between 0.001 and 0.05.

The possible additives include silicas. Hence the composition may comprise more particularly one or more hydrophilic or hydrophobic silicas or mixtures thereof.

Hydrophilic silicas in the sense of the present invention are not only pure hydrophilic silicas but also particles which are wholly or partly coated with hydrophilic silica.

The hydrophilic silicas which can be used in the composition of the invention are preferably amorphous.

They are generally in powder form.

They may also be pyrogenic or precipitated in origin.

Fumed (pyrogenic) silicas are obtained typically by continuous flame pyrolysis at 1000° C. of silicon tetrachloride ($SiCl_4$) in the presence of hydrogen and oxygen.

Precipitated silicas are obtained more particularly by reaction of an acid with solutions of alkali metal silicates, preferably sodium silicate.

According to one preferred embodiment of the invention the hydrophilic silica is selected from silicas having a specific surface area of 30 to 500 $m^2/g$ and a number-average particle size of from 3 to 50 nm.

These are more particularly the hydrophilic silicas described in tables (1) and (2) below, and mixtures thereof.

TABLE (1)

| | Trade name | | | |
|---|---|---|---|---|
| | AEROSIL 90 (Degussa-Hüls) | AEROSIL 130 (Degussa-Hüls) | AEROSIL 150 (Degussa-Hüls) | AEROSIL 200 (Degussa-Hüls) |
| Preparation method | Pyrolysis | Pyrolysis | Pyrolysis | Pyrolysis |
| BET surface area ($m^2/g$) | 90 ± 15 | 130 ± 25 | 150 ± 15 | 200 ± 15 |
| Average particle size (nm) | 20 | 16 | 14 | 12 |

Remarks
aggregate size: 10-30 μm and 200 μm

TABLE (2)

| | Trade name | | | |
|---|---|---|---|---|
| | AEROSIL 300 (Degussa-Hüls) | AEROSIL 380 (Degussa-Hüls) | AEROSIL OX 50 (Degussa-Hüls) | SILICE FK 320 DS (Degussa-Hüls) |
| Preparation method | Pyrolysis | Pyrolysis | Pyrolysis | Precipitation |
| BET surface area ($m^2/g$) | 300 ± 30 | 380 ± 30 | 50 ± 25 | 170 ± 25 |
| Average particle size (nm) | 7 | 7 | 40 | 18 |

NB: the +/− gives the range of variation of the BET surface area

The hydrophilic silica employed in the composition according to the invention may also be composed of a particle, in particular an inorganic particle, which is wholly or partly covered with silica.

Mention may be made in particular of the silica beads containing titanium oxide that are sold under the name Torayceram S-IT® by Toray; the silica-alumina microspheres containing titanium oxide (size: 105 μm) that are sold under the name Z-LIGHT-SPHERE W 1012® by Zeelan; the amorphous precipitated synthetic silica/titanium oxide particles (size: 106-500 μm) that are sold under the name Neosil PC20S® by Crosfield; the nylon 6/silica/titanium oxide fibres (length of 2 mm and thickness of 2 denier) that are sold under the name Fiberlon Y2® by Wackherr; the silica that is coated with titanium dioxide and covered with porous silica (85/5/10) (size: 0.6 μm) that is sold under the name ACS-0050510® by SACI-CFPA; the anatase titanium oxide nanomaterial treated with alumina and silica, at 40% in water (size: 60 nm, monodisperse), that is sold under the name Mirasun TIW 60® by Rhodia Chimie; the anatase titanium oxide nanomaterial (60 nm) coated with 15/5/3 silica/alumina/cerium IV in aqueous dispersion at 32% that is sold under the name Mirasun TIW 160® by Rhodia Chimie; the anatase titanium oxide nanomaterial treated with alumina and silica (34/4.3/1.7) in aqueous dispersion at 40% that is sold under the name Tioveil AQ-N® by Uniqema; the titanium oxide nanomaterial coated with silica (66/33) (particle size of the titanium dioxide: 30 nm; thickness of silica: 4 nm) that is sold under the name Maxlight TS-04® by Nichimen Europe PLC; and the titanium oxide nanomaterial coated with silica (80/20) (particle size of the titanium dioxide: 30 nm; thickness of silica: 2 nm) that is sold under the name Maxlight TS-042® by Nichimen Europe PLC.

As hydrophilic silica it is preferred to use fumed silicas and especially those sold under the name Aerosil (INCI name: silica) and more particularly that sold under the name Aerosil 200 by Degussa-Hüls.

Hydrophobic silicas in the sense of the present invention are not only pure hydrophobic silicas but also particles wholly or partly coated with hydrophobic silica.

The hydrophobic silicas that can be used in the composition of the invention are preferably amorphous and pyrogenic in origin.

They are preferably in powder form.

The amorphous hydrophobic silicas of pyrogenic origin are obtained more particularly from hydrophilic silicas. The latter are obtained by continuous flame pyrolysis at 1000° C. of silicon tetrachloride ($SiCl_4$) in the presence of hydrogen and oxygen. They are then made hydrophobic by treatment with halogenated silanes, alkoxysilanes or silazanes. The hydrophobic silicas differ from the hydrophilic starting silicas in qualities including a lower density of silanol groups and a smaller level of water vapour adsorption.

According to one preferred embodiment of the invention the hydrophobic silica is selected from silicas having a specific surface area of 50 to 500 $m^2/g$ and a number-average particle size of from 3 to 50 nm.

These are, more particularly, the hydrophobic silicas described in table (3) below, and mixtures thereof.

TABLE (3)

| | Trade name | | | | |
|---|---|---|---|---|---|
| | AEROSIL R202 (Degussa-Hüls) | AEROSIL R805 (Degussa-Hüls) | AEROSIL R812 (Degussa-Hüls) | AEROSIL R972 (Degussa-Hüls) | AEROSIL R974 (Degussa-Hüls) |
| BET surface area ($m^2/g$) | 90 ± 20 | 150 ± 25 | 260 ± 30 | 110 ± 20 | 170 ± 20 |
| Average particle size (nm) | 14 | 12 | 7 | 16 | 12 |

The hydrophobic silica used in the composition according to the invention may also consist of a particle, in particular an inorganic particle, such as pigments and metal oxides, that are wholly or partly covered with hydrophobic silica.

These particles may also have optical effects in the product, such as on the hair; for example, they may have a dulling or slightly whitening effect.

As hydrophobic silica it is preferred to use a hydrophobic fumed silica which is surface-treated with a dimethylsiloxane, such as that sold under the name Aerosil R972 (INCI name: Silica Dimethyl Silylate) by Degussa-Hüls.

The silicas used in the invention are preferably hydrophobic silicas.

Preferably, if the composition comprises silica, its amount represents from 0.1% to 10% by weight, more particularly from 0.5% to 5% by weight, and even more preferably from 1% to 3% by weight, relative to the composition weight.

In accordance with one particularly advantageous variant of the invention, and when the composition comprises silica, the silica/ammonium chloride mass ratio is preferably between 0.01 and 2, advantageously between 0.1 and 1 and even more preferably between 0.2 and 0.8.

The additives that may be contemplated include ascorbic acid and its salts, such as, for example, salts of alkali metals such as sodium and potassium, of alkaline-earth metals such as calcium, of ammonium, of primary, secondary or tertiary amines containing one to three identical or different $C_1$-$C_4$ alkyl groups optionally carrying a hydroxyl group.

Preferably, if the composition comprises ascorbic acid, in acid and/or salt form, its amount, expressed in acid form, represents from 0.01% to 10% by weight, more particularly from 0.05% to 5% by weight and preferably from 0.1% to 1% by weight, relative to the composition weight.

In accordance with one particularly advantageous variant of the invention, and when the composition comprises ascorbic acid, in acid and/or salt form, the ascorbic acid (expressed in acid form)/ammonium chloride mass ratio is preferably between 0.5 and 0.005 and even more preferably between 0.2 and 0.01.

The composition according to the invention may also comprise one or more fatty acids.

The term "fatty acid" denotes compounds comprising at least one carboxyl function in free form and a linear or branched, saturated or unsaturated hydrocarbon chain containing 8 to 40, preferably 8 to 30, carbon atoms, which optionally carries one or more hydroxyl groups, preferably 1 or 2 hydroxyl groups. If the fatty acid is unsaturated, it may comprise, in particular, from one to four conjugated or non-conjugated carbon-carbon double bonds.

The possible fatty acids include caprylic, lauric, myristic, palmitic, cetylic, stearic, behenic, arachidic, oleic, linoleic, linolenic, arachidonic and erucic acids, or mixtures thereof, such as cetylstearylic acid.

Preferably the fatty acid is a saturated acid.

These fatty acids may be converted to salt form. Salts include in particular the salts of alkali metals, such as sodium and potassium, of alkaline-earth metals such as calcium, of ammonium, of primary, secondary or tertiary amines containing one to three identical or non-identical $C_1$-$C_4$ alkyl groups optionally carrying a hydroxyl group.

Advantageously, if the composition comprises one or more fatty acids, in acid and/or salt form, their total amount, expressed in acid form, represents from 0.1% to 20% by weight, more particularly from 0.5% to 15% by weight and even more advantageously from 1% to 10% by weight, relative to the composition weight.

In accordance with one particularly advantageous variant of the invention, and when the composition comprises one or more fatty acids, the fatty acid (expressed in acid form)/ammonium chloride mass ratio is preferably between 0.01 and 10, more particularly between 0.1 and 5 and even more preferably between 0.2 and 2.

The composition according to the invention may optionally comprise one or more alkanolamines as additives.

An alkanolamine in the sense of the present invention is a compound containing a linear or branched hydrocarbon chain that carries one or more hydroxyl groups and one or more amino groups, it being possible for the latter to be optionally substituted.

Preferably the alkanolamines are of structure (C)

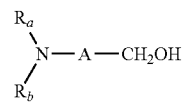

where $R_a$ and $R_b$ denote independently of one another a hydrogen atom, a linear or branched $C_1$-$C_{10}$ and preferably $C_1$-$C_4$ alkyl radical or a linear or branched $C_1$-$C_{10}$ and preferably $C_1$-$C_4$ mono- or polyhydroxyalkyl radical;

A denotes a linear or branched $C_1$-$C_{10}$, preferably $C_1$-$C_4$, alkylene radical which is optionally substituted by one or more hydroxyl radicals.

Alkanolamines include monoethanolamine, di-ethanolamine, triethanolamine, monoisopropanolamine, diisopropanolamine, triisopropanolamine, N,N-di-methylethanolamine, N,N-diethylethanolamine, 2-amino-2-methyl-1-propanol, 2-amino-2-methyl-1,3-propanediol and 2-amino-2-hydroxymethyl-1,3-propanediol.

Preferably the alkanolamine is monoethanolamine.

It should be noted that the alkanolamine may be in free form or in the form of a salt with an acid compound, such as, for example, the aforementioned ascorbic acid and fatty acids, the crosslinked polyacrylic acid detailed later on below, and also hydrochloric, hydrobromic, sulphuric, phosphoric, acetic, citric, succinic, tartaric, lactic, toluenesulphonic and benzenesulphonic acids.

In particular, if the composition comprises one or more alkanolamines, their total amount, expressed in free form, represents from 0.1% to 15% by weight, more particularly from 0.5% to 12% by weight and preferably from 1% to 10% by weight, relative to the composition weight.

In accordance with one preferred variant of the invention, and when the composition comprises one or more alkanolamines, the amount of ammonium chloride is between 2% and 5% by weight, relative to the weight of the composition.

Moreover, according to this variant, the amount of aqueous ammonia, expressed in terms of gaseous ammonia, is between 0.5% and 2% by weight, relative to the weight of the composition.

In accordance with one particularly advantageous variant of the invention, and when the composition comprises one or more alkanolamines, the alkanolamines (expressed in non-salt form)/ammonium chloride mass ratio is preferably between 0.01 and 5, more particularly between 0.05 and 1 and even more preferably between 0.1 and 0.5.

The composition according to the invention may comprise, as an additive, one or more crosslinked homopolymers of acrylic acid, in free form or in the form of salts, such as, for example, salts of alkali metals such as sodium or potassium, of alkaline-earth metals such as calcium, of ammonium, of primary, secondary or tertiary amines containing one to three identical or non-identical $C_1$-$C_4$ alkyl groups optionally carrying a hydroxyl group, preferably of monoethanolamine.

It may be wholly or partly crosslinked, with an allyl ether, for example.

It may, for example, be an acrylic acid homopolymer crosslinked with a pentaerythritol allyl ether, with a sucrose allyl ether or with a propylene allyl ether. Polymers of this kind are classed in particular under the Carbomer name in the CTFA dictionary, 9th edition, 2002. They are sold under names which include Carbopol by Noveon and Synthalen by 3V Inc.

The molecular weight of the acrylic acid homopolymers employed in the context of the invention is more particularly greater than or equal to 100 000 g/mol. Preferably it is greater than or equal to 500 000 g/mol and, more advantageously, is greater than or equal to 1 000 000 g/mol. Very particularly it is between 1 000 000 g/mol and 10 000 000 g/mol.

Advantageously, if the composition comprises one or more acrylic acid homopolymers, their amount, expressed in terms of polyacrylic acid, represents from 0.05% to 5% by weight, more advantageously from 0.1% to 3% by weight and preferably from 0.2% to 1% by weight, relative to the composition weight.

In accordance with one particularly advantageous variant of the invention, and when the composition comprises one or more acrylic acid homopolymers, the acrylic acid homopolymers (expressed in terms of polyacrylic acid)/ammonium chloride mass ratio is preferably between 0.01 and 1, more particularly between 0.05 and 0.75 and even more preferably between 0.1 and 0.5.

The composition may also comprise one or more copolymers of dialkyldiallylammonium chloride and acrylic acid.

In particular the said polymer comprises at least one unit of formula

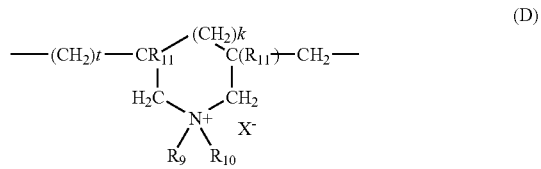

(D)

in which k and t are 0 or 1, the sum k+t being 1;

$R_9$ and $R_{10}$, which are identical or different, denote a $C_1$-$C_{26}$ alkyl group, a hydroxyalkyl($C_1$-$C_5$) group, an alkyl($C_1$-$C_2$) amidoalkyl($C_1$-$C_4$) group, or $R_9$ and $R_{10}$, jointly with the nitrogen atom to which they are attached, denote a piperidinyl or morpholinyl group;

$R_{11}$ denotes a hydrogen atom or a methyl radical; and
$X^-$ is an anion.

Preferably $R_9$ and $R_{10}$ denote methyl.

These polymers may optionally include in their structure units obtained from other monomers such as, for example, acrylamide.

Polymers of this kind are in particular classed under the Polyquaternium-22 and Polyquaternium-39 names in the CTFA dictionary, 9th edition, 2002.

They are sold, for example, by Ondeo Nalco under the names Merquat 295 and Merquat 280 for Polyquaternium-22 and Merquat Plus 3330 and Merquat Plus 3331 for Polyquaternium-39.

Advantageously, if the composition comprises one or more copolymers of this type, their total amount represents from 0.1% to 10% by weight, more particularly from 0.2% to 5% and preferably from 0.5% to 2% by weight, relative to the composition weight.

In accordance with one particularly advantageous variant of the invention, and when the composition comprises one or more copolymers of dialkyldiallyl-ammonium chloride and acrylic acid, the copolymer/ammonium chloride mass ratio is preferably between 0.05 and 1, more particularly between 0.1 and 0.8 and even more preferably between 0.2 and 0.5.

The composition according to the invention may also comprise one or more cationic polymers composed of repeat units of formula (A) below

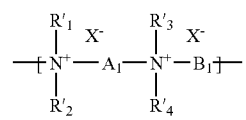

in which $R'_1$, $R'_2$, $R'_3$ and $R'_4$, which are identical or different, represent aliphatic, alicyclic or aryl aliphatic groups containing 1 to 6 carbon atoms, or aliphatic hydroxy($C_1$-$C_6$)alkyl groups, or else $R'_1$, $R'_2$, $R'_3$ and $R'_4$, together or separately, constitute, with the nitrogen atoms to which they are attached, saturated heterocycles having five or six members, optionally comprising a second heteroatom other than nitrogen (for example oxygen or sulphur), or else $R'_1$, $R'_2$, $R'_3$ and $R'_4$ represent a linear or branched $C_1$-$C_6$ alkyl group substituted by a nitrile, ester, acyl, amide or —CO—O—$R'_5$-D or —CO—NH—$R'_5$-D group where $R'_5$ is a $C_1$-$C_6$ alkylene group and D is a quaternary ammonium group containing $C_1$-$C_6$ alkyl groups which are identical or not;

$A_1$ and $B_1$ represent polymethylene groups containing 2 to 6 carbon atoms, which may be linear or branched, saturated or unsaturated, and may contain, bonded to (substituent) or intercalated in the main chain, a $C_6$ aromatic ring, or an oxygen or sulphur atom, or sulphoxide, sulphone, disulphide, amino, alkylamino, hydroxyl, quaternary ammonium, ureido or ester groups, or combinations thereof, and $X^-$ denotes an anion derived from an organic or inorganic acid;

$A_1$, $R'_1$ and $R'_3$ may form, with the two nitrogen atoms to which they are attached, a piperazine ring.

In the formula above, preferably, $X^-$ is an anion selected from bromide, chloride, acetate, borate, citrate, tartrate, bisulphate, bisulphite, sulphate and phosphate ions, and preferably chloride and bromide ions.

Polymers of this type are described in particular in French patents numbers 2 320 330, 2 270 846, 2 316 271, 2 336 434 and 2 413 907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

It is possible more particularly to use the polymers which are composed of repeat units corresponding to the formula:

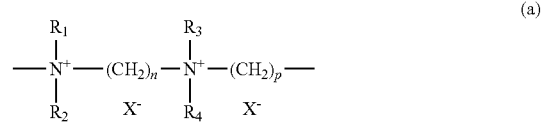

(a)

in which $R_1$, $R_2$, $R_3$ and $R_4$, which are identical or different, denote an alkyl or hydroxyalkyl group having about 1 to 4 carbon atoms, n and p are whole numbers ranging from about 2 to 6, and X⁻ is an anion derived from an organic or inorganic acid as defined earlier on above.

One particularly preferred compound of formula (a) is that for which $R_1$, $R_2$, $R_3$ and $R_4$ represent a methyl group and n=3, p=6 and X=Cl, in other words the compound named "Hexadimethrine chloride" in accordance with the INCI (CTFA) nomenclature.

According to one particular embodiment the polycondensate useful in the present invention has a cationic charge of more than 5 meq/g, preferably of more than 6 meq/g. This charge density may be determined either by calculation from the structure of the polymer or experimentally by the Kjeldahl method.

Advantageously, if the composition comprises one or more cationic polymers with repeat units (A), their total amount represents from 0.1% to 10% by weight, more particularly from 0.2% to 5% and preferably from 0.5% to 3% by weight, relative to the composition weight.

In accordance with one particularly advantageous variant of the invention, and when the composition comprises one or more polymers of this type, the cationic polymer with repeat units (A)/ammonium chloride mass ratio is between 0.05 and 10, more particularly between 0.1 and 5 and preferably between 0.2 and 1.

The compositions of the invention preferably contain one or more additives selected from fatty acids and/or salts thereof, alkanolamines and/or salts thereof, copolymers of dialkyldiallylammonium chloride and acrylic acid and the cationic polymers composed of repeat units of formula A described above.

According to one particular embodiment the composition comprises one or more surfactants. These surfactants may be selected, alone or in mixtures, from anionic, amphoteric, nonionic, zwitterionic and cationic surfactants, and more preferably from anionic or nonionic surfactants.

With regard to the anionic surfactants it is common to use salts, especially the salts of alkali metals such as sodium salts, ammonium salts, amine salts, salts of amino alcohols or salts of alkaline-earth metals, for example, magnesium salts, of the following compounds, alone or in a mixture:

alkyl sulphates, alkyl ether sulphates, alkylamido ether sulphates and alkylaryl polyether sulphates;
  alkylsulphonates, alkylamidesulphonates, alkylaryl-sulphonates;
  alkylsulphosuccinates, alkyl ether sulphosuccinates, alkylamide-sulphosuccinates;
  alkyl sulphoacetates;
  acylsarcosinates; and acylglutamates;
  alkyl polyglycoside-carboxylate esters, such as alkyl glucoside-citrates, alkyl polyglycoside-tartrates and alkyl polyglycoside-sulphosuccinates;
  alkylsulphosuccinamates;
  acylisethionates, N-acyltaurates; acyllactylates;
  alkyl-D-galactoside uronates;
  polyoxyalkylenated alkyl ether carboxylates, polyoxyalkylenated alkylaryl ether carboxylates and polyoxyalkylenated alkylamido ether carboxylates;

in these compounds the alkyl or acyl group (RCO—) contains 10 to 24 carbon atoms and the aryl group denotes preferably a phenyl or benzyl group; the number of oxyalkylenated groups, and preferably oxyethylenated groups, is between 2 and 50.

Preferably the anionic surfactants, if present, are selected from alkyl sulphates, alkyl ether sulphates, alkylamido ether sulphates, alkylsulphonates, acylisethionates, N-acyltaurates, polyoxyalkylenated alkyl ether carboxylates and polyoxyalkylenated alkylamido ether carboxylates; in these compounds, the alkyl or acyl group (RCO—) contains 10 to 24 carbon atoms and the aryl group preferably denotes a phenyl or benzyl group; the number of oxyalkylenated groups, and preferably oxyethylenated groups, is between 2 and 50.

With regard to the nonionic surfactants, they may be advantageously selected from the following compounds, alone or in a mixture:

polyethoxylated, polypropoxylated and/or poly-glycerolated fatty alcohols,
  polyethoxylated, polypropoxylated and/or poly-glycerolated alpha-diols, the number of ethylene oxide or propylene oxide groups ranging from 2 to 50 and the number of glycerol groups ranging from 2 to 30;

polyethoxylated fatty amides having 2 to 30 mol of ethylene oxide;
  polyglycerolated fatty amides containing 1 to 5 glycerol groups;
  ethoxylated esters of fatty acids of sorbitan, having 2 to 30 mol of ethylene oxide, and fatty acid esters of sucrose;
  alkylpolyglucosides, N-alkylglucamine derivatives; these compounds containing at least one fatty chain of alkyl or alkenyl type or at least one alkyl or alkenyl chain containing 10 to 24 carbon atoms;
  copolymers of ethylene oxide and propylene oxide.

Preferably the nonionic surfactants, if present, are selected from polyethoxylated or polyglycerolated fatty alcohols, polyethoxylated fatty amides having 2 to 30 mol of ethylene oxide; polyglycerolated fatty amides containing 1 to 5 glycerol groups; these compounds containing at least one fatty chain of alkyl or alkenyl type containing 10 to 24 carbon atoms.

Typically, if they are present, the surfactant or surfactants represent an amount of between 0.01% and 50% by weight, preferably between 0.1% and 25% by weight, relative to the weight of the composition.

The dyeing composition in accordance with the invention may also include various adjuvants which are conventionally used in compositions for dyeing hair, such as, for example, thickeners other than the crosslinked homopolymers of acrylic acid, such as cellulosic thickeners (with, for example, hydroxyethylcellulose, hydroxypropylcellulose, carboxymethylcellulose), guar gum and its derivatives (for example hydroxypropylguar), gums of microbial origin (especially xanthan gum or scleroglucan gum); inorganic thickeners such as, in particular, clays; antioxidants or reducing agents other than ascorbic acid, such as, for example, erythorbic acid, ammonium sulphite, bisulphite or metabisulphite, and ammonium thiolactate; penetrants, sequestrants such as ethylenediaminetetraacetic acid or its salts; fragrances; titanium oxides; buffers; dispersants; film-forming agents other than the cationic polymers described above; direct dyes which are synthetic or of natural origin; and preservatives.

The above adjuvants are generally present in an amount, for each of them, of between 0.01% and 20% by weight, relative to the weight of the composition.

The cosmetically acceptable medium of the composition, which is a medium appropriate for the colouring of human keratin fibres, preferably comprises water and one or more solvents.

Examples of such solvents include linear or branched $C_2$-$C_4$ alkanols, such as ethanol and isopropanol; polyols and polyol ethers such as 2-butoxyethanol, hexylene glycol, propylene glycol, dipropylene glycol, propylene glycol monomethyl ether, diethylene glycol monoethyl and monomethyl ether, and glycerol, and also aromatic alcohols such as benzyl alcohol, benzyloxyethanol or phenoxyethanol, and mixtures thereof.

The solvent or solvents may be present in proportions of from 1% to 40% by weight, relative to the weight of the composition, and preferably from 5% to 30% by weight.

The pH of the composition according to the invention, devoid of oxidizing agent, is typically between 6 and 11.5.

With particular advantage it is greater than or equal to 9.2. This pH is preferably between 9.2 to 11, more particularly between 9.3 to 10 and even more preferably between 9.4 to 9.9.

For the purposes of the invention, specifying that the colouring (or dyeing) composition does not contain an oxidizing agent means that it does not comprise any chemical oxidizing agent, and in particular no chemical oxidizing agent selected from hydrogen peroxide, urea peroxide, the bromates or ferricyanides of alkali metals, and peroxygenated salts such as, for example, the persulphates, perborates and percarbonates of alkali metals or alkaline-earth metals, such as sodium, potassium and magnesium.

The pH may be adjusted to the desired value by means of the ammonium chloride and the aqueous ammonia and, optionally, of one or more acidifying agents or one or more alkalifying agents which are typically used in the field.

The acidifying agents include, for example, organic or inorganic acids such as hydrochloric acid, orthophosphoric acid, sulphuric acid, carboxylic acids such as acetic acid, tartaric acid, citric acid and lactic acid, and sulphonic acids.

The alkalifying agents include, for example, alkali metal carbonates, the aforementioned alkanolamines, sodium hydroxide or potassium hydroxide, and the compounds of formula:

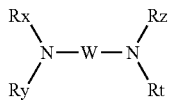

in which W is a propylene residue optionally substituted by a hydroxyl group or a $C_1$-$C_6$ alkyl radical, and Rx, Ry, Rz and Rt, which are identical or different, represent a hydrogen atom or a $C_1$-$C_6$ alkyl or $C_1$-$C_6$ hydroxyalkyl radical.

The composition according to the invention may be mixed with one or more oxidizing agents. In this case it is referred to as a ready-to-use composition.

In particular the ready-to-use composition is obtained by extemporaneous mixing, prior to application, of a composition devoid of oxidizing agent as described above with at least one composition comprising one or more oxidizing agents.

The oxidizing agent is selected preferably from hydrogen peroxide, urea peroxide, the bromates or ferricyanides of alkali metals, peroxygenated salts such as, for example, the persulphates, perborates and percarbonates of alkali metals or alkaline-earth metals, such as sodium, potassium and magnesium.

The use of hydrogen peroxide is particularly preferred.

This oxidizing agent is advantageously composed of hydrogen peroxide in aqueous solution with a content which can vary, more particularly, from 1 to 40 volumes, and even more preferably from 5 to 40 volumes.

The compositions according to the invention may result from the extemporaneous mixing of two or more compositions.

The invention thus further provides a method of colouring human keratin fibres by applying the composition described above, in the presence of one or more oxidizing agents.

According to a first variant of this embodiment, the ready-to-use composition which has just been detailed, and which is therefore obtained by extemporaneous mixing, prior to application, of a composition according to the invention devoid of oxidizing agent with an oxidizing composition, is applied to the fibres.

The colouring composition without oxidizing agent and the oxidizing composition are mixed preferably in a colouring composition without oxidizing agent/oxidizing composition weight ratio of from 2 to 0.25 and preferably from 1 to 0.5.

The pH of the ready-to-use composition resulting from the mixing is preferably from 7.5 to 10, better still from 8 to 9.8 and even more preferably from 8.5 to 9.5.

According to a second variant of this embodiment, the composition according to the invention devoid of oxidizing agent, and an oxidizing composition are applied in succession and without rinsing in between.

The oxidizing composition employed comprises one or more oxidizing agents as defined above.

With regard to the organic solvents optionally present in the oxidizing composition, reference may be made to the list given above in the context of the description of the composition according to the invention.

Typically the pH of the oxidizing composition is less than 7.

The oxidizing composition may take the form of a solution, an emulsion or a gel.

It may optionally comprise one or more additives which are conventionally used in the field of the colouring of human keratin fibres, depending on the desired presentation form. There again, reference may be made to the list of additives given earlier on above.

Irrespective of the embodiment employed (simultaneous or successive application), the mixture applied to the fibres is left in place for a time, in general, of the order of 5 minutes to 60 minutes, preferably of 5 minutes to 30 minutes and even more advantageously of 5 minutes to 20 minutes.

The temperature during the method is conventionally between 10 and 200° C. and more particularly between ambient temperature (between 15 to 25° C.) and 80° C., preferably between ambient temperature and 60° C.

At the end of the treatment, the human keratin fibres are optionally rinsed with water, optionally washed with shampoo and rinsed again with water, and then dried or left to dry.

The invention lastly provides a multiple-compartment device of which at least one compartment comprises the composition according to the invention, devoid of oxidizing agent, and at least one second compartment comprises at least one oxidizing composition, comprising one or more oxidizing agents.

Specific examples which do not, however, limit the invention will now be presented.

EXAMPLES

In the examples which follow, in the absence of any indication to the contrary, the amounts are expressed in % by weight of active substance.

Example 1

This example illustrates a composition according to the invention comprising a ceramide as additive.

The composition below is prepared.

| | |
|---|---|
| lauric acid monoisopropanolamide | 3 |
| ethoxylated lauryl alcohol (12 EO) | 7 |
| ethoxylated oleocetyl alcohol (30 EO) | 4 |
| ethoxylated decyl alcohol (3 EO) | 10 |
| cetylstearyl alcohol (C16-C18 - 50/50) | 11.5 |
| diethylene triamine pentacetic acid, pentasodium salt, in aqueous solution at 40% | 4 |
| kaolin | 1.2 |
| 1,3-diaminopropane | 0.4 |
| Polyquaternium 6 | 4 |
| 2-oleamido-1,3-octadecanediol (ceramide) | 0.01 |
| propylene glycol | 7 |
| Carbopol ETD 2020 | 0.6 |
| ammonium chloride | 3.78 |
| titanium oxide | 0.15 |
| sequestrant | q.s |
| reducing agents | q.s |
| antioxidants | q.s |
| fragrance | 0.6 |
| aqueous ammonia (containing 20.5% ammonia) | 6 |
| para-toluenediamine | 1.8 |
| 1-beta-hydroxyethyloxy-2,4-diaminobenzene dihydrochloride | 0.03 |
| 2-methyl-1,3-dihydroxybenzene | 0.6 |
| meta-aminophenol | 0.4 |
| resorcinol | 1 |
| deionized water (qs) | 100 |

The composition is then mixed with a 30-volume oxidizing composition (dilution 1 to 1 by weight).

The resulting mixture is applied to locks of natural hair containing 90% of white hairs.

The mixture is left to take for 10 minutes at ambient temperature (23° C.+/−3° C.).

At the end of this application time, the locks are rinsed with water, washed with a standard shampoo and then dried.

This gives a light brown shade with a good quality of the fibre.

Example 2

This example illustrates a composition comprising a particular cationic polymer (Mexomere PO).

The composition below is prepared:

| | |
|---|---|
| lauric acid monoisopropanolamide | 3 |
| ethoxylated lauryl alcohol (12 EO) | 7 |
| ethoxylated oleocetyl alcohol (30 EO) | 4 |
| ethoxylated decyl alcohol (3 EO) | 10 |
| cetylstearyl alcohol (C16-C18 - 50/50) | 11.5 |
| kaolin | 1.2 |
| 1,3-diaminopropane | 0.4 |
| diethylene triamine pentacetic acid, pentasodium salt, in aqueous solution at 40% | 4 |
| Mexomere PO | 3 |
| propylene glycol | 7 |
| crosslinked polyacrylic acid | 0.6 |
| ammonium chloride | 3.78 |
| titanium oxide | 0.15 |
| sequestrant | q.s |
| reducing agents | q.s |
| antioxidants | q.s |
| fragrance | 0.6 |
| aqueous ammonia (containing 20.5% ammonia) | 6 |
| N,N-bis(2-hydroxyethyl)-p-phenylenediamine sulphate, 1 $H_2O$ | 0.25 |
| resorcinol | 1.3 |
| 1-hydroxy-3-aminobenzene | 0.3 |
| para-phenylenediamine | 1.8 |
| deionized water (qs) | 100 |

The composition is then mixed with a 30-volume oxidizing composition (dilution 1 to 1 by weight).

The resulting mixture is applied to locks of natural hair containing 90% of white hairs.

The mixture is left to take for 10 minutes at ambient temperature (23° C.+/−3° C.).

At the end of this application time, the locks are rinsed with water, washed with a standard shampoo and then dried.

This gives a brown shade with a good quality of the fibre.

Example 3

This example illustrates a composition comprising silica.

The composition below is prepared:

| | |
|---|---|
| lauric acid monoisopropanolamide | 3 |
| ethoxylated lauryl alcohol (12 EO) | 7 |
| ethoxylated oleocetyl alcohol (30 EO) | 4 |
| ethoxylated decyl alcohol (3 EO) | 10 |
| cetylstearyl alcohol (C16-C18 - 50/50) | 11.5 |
| hydrophobic fumed silica | 1.2 |
| 1,3-diaminopropane | 0.4 |
| diethylene triamine pentacetic acid, pentasodium salt, in aqueous solution at 40% | 4 |
| Polyquaternium 6 | 4 |
| propylene glycol | 7 |
| Carbopol ETD 2020 | 0.6 |
| ammonium chloride | 3.78 |
| titanium oxide | 0.15 |
| sequestrants | q.s |
| reducing agents | q.s |
| antioxidants | q.s |
| fragrance | 0.6 |
| aqueous ammonia (containing 20.5% ammonia) | 6 |
| N,N-bis(2-hydroxyethyl)-p-phenylenediamine sulphate, 1 $H_2O$ | 0.2 |
| resorcinol | 1.3 |
| 1-hydroxy-3-aminobenzene | 0.3 |
| para-phenylenediamine | 1.8 |
| deionized water (qs) | 100 |

The composition is then mixed with a 30-volume oxidizing composition (dilution 1 to 1 by weight).

The resulting mixture is applied to locks of natural hair containing 90% of white hairs.

The mixture is left to take for 10 minutes at ambient temperature (23° C.+/−3° C.).

At the end of this application time, the locks are rinsed with water, washed with a standard shampoo and then dried.

This gives a brown shade with a good quality of the fibre.

Example 4

This example illustrates a composition comprising Polyquaternium-22.

The composition below is prepared:

| | |
|---|---|
| lauric acid monoisopropanolamide | 3 |
| ethoxylated lauryl alcohol (12 EO) | 7 |
| ethoxylated oleocetyl alcohol (30 EO) | 4 |
| ethoxylated decyl alcohol (3 EO) | 10 |
| cetylstearyl alcohol (C16-C18 - 50/50) | 11.5 |
| diethylene triamine pentacetic acid, pentasodium salt, in aqueous solution at 40% | 4 |
| hydrophobic fumed silica | 1.2 |
| 1,3-diaminopropane | 0.4 |
| Polyquaternium 22 | 3 |
| propylene glycol | 7 |
| Carbopol ETD 2020 | 0.6 |

-continued

| | |
|---|---|
| ammonium chloride | 3.78 |
| titanium oxide | 0.15 |
| sequestrants | q.s |
| reducing agents | q.s |
| antioxidants | q.s |
| fragrance | 0.6 |
| aqueous ammonia (containing 20.5% ammonia) | 6 |
| para-toluenediamine | 1.1 |
| 2-methylresorcinol | 0.3 |
| 6-hydroxyindole | 0.03 |
| resorcinol | 0.6 |
| meta-aminophenol | 0.1 |
| para-aminophenol | 0.09 |
| deionized water (qs) | 100 |

The composition is then mixed with a 30-volume oxidizing composition (dilution 1 to 1 by weight).

The resulting mixture is applied to locks of natural hair containing 90% of white hairs.

The mixture is left to take for 10 minutes at ambient temperature (23° C.+/−3° C.).

At the end of this application time, the locks are rinsed with water, washed with a standard shampoo and then dried.

This gives a very light brown shade with a good quality of the fibre.

Example 5

This example illustrates a composition comprising a crosslinked homopolymer of acrylic acid.

The composition below is prepared:

| | |
|---|---|
| lauric acid monoisopropanolamide | 3 |
| ethoxylated lauryl alcohol (12 EO) | 7 |
| ethoxylated oleocetyl alcohol (30 EO) | 4 |
| ethoxylated decyl alcohol (3 EO) | 10 |
| cetylstearyl alcohol (C16-C18 - 50/50) | 11.5 |
| diethylene triamine pentacetic acid, pentasodium salt, in aqueous solution at 40% | 4 |
| kaolin | 1.2 |
| 1,3-diaminopropane | 0.4 |
| Polyquaternium 6 | 4 |
| propylene glycol | 7 |
| crosslinked polyacrylic acid (Carbomer 980) | 0.6 |
| ammonium chloride | 3.78 |
| titanium oxide | 0.15 |
| sequestrants | q.s |
| reducing agents | q.s |
| antioxidants | q.s |
| fragrance | 0.6 |
| aqueous ammonia (containing 20.5% ammonia) | 6 |
| para-toluenediamine | 2 |
| 2,4-diaminophenoxyethanol HCl | 0.02 |
| 2-methylresorcinol | 0.76 |
| meta-aminophenol | 0.3 |
| resorcinol | 1 |
| para-aminophenol | 0.2 |
| deionized water (qs) | 100 |

The composition is then mixed with a 30-volume oxidizing composition (dilution 1 to 1 by weight).

The resulting mixture is applied to locks of natural hair containing 90% of white hairs.

The mixture is left to take for 10 minutes at ambient temperature (23° C.+/−3° C.).

At the end of this application time, the locks are rinsed with water, washed with a standard shampoo and then dried.

This gives a golden brown shade with a good quality of the fibre.

Example 6

This example illustrates two compositions comprising monoethanolamine.

The compositions below are prepared:

| | | |
|---|---|---|
| lauric acid monoisopropanolamide | 3 | 3 |
| ethoxylated lauryl alcohol (12 EO) | 7 | 7 |
| ethoxylated oleocetyl alcohol (30 EO) | 4 | 4 |
| ethoxylated decyl alcohol (3 EO) | 10 | 10 |
| cetylstearyl alcohol (C16-C18 - 50/50) | 11.5 | 11.5 |
| diethylene triamine pentacetic acid, pentasodium salt, in aqueous solution at 40% | 4 | 4 |
| kaolin | 1.2 | 1.2 |
| pure monoethanolamine | 0.4 | 1.6 |
| Polyquaternium 6 | 4 | 4 |
| propylene glycol | 7 | 7 |
| Carbopol ETD 2020 | 0.6 | 0.6 |
| ammonium chloride | 3.78 | 3.78 |
| titanium oxide | 0.15 | 0.15 |
| sequestrants | q.s | q.s |
| reducing agents | q.s | q.s |
| antioxidants | q.s | q.s |
| fragrance | 0.6 | 0.6 |
| aqueous ammonia (containing 20.5% ammonia) | 6 | 6 |
| para-toluenediamine | 0.9 | 0.9 |
| 2,4-diaminophenoxyethanol HCl | 0.05 | 0.05 |
| 2-methylresorcinol | 0.6 | 0.6 |
| para-aminophenol | 0.8 | 0.8 |
| meta-aminophenol | 0.15 | 0.15 |
| resorcinol | 0.5 | 0.5 |
| 6-hydroxyindole | 0.15 | 0.15 |
| 2-methyl-5-hydroxyethylaminophenol | 0.3 | 0.3 |
| deionized water (qs) | 100 | 100 |

Then each composition is mixed with a 30-volume oxidizing composition (dilution 1 to 1 by weight).

Each of the resulting mixtures is applied to locks of natural hair containing 90% white hair.

The mixture is left to take for 10 minutes at ambient temperature (23° C.+/−3° C.).

At the end of this application time, the locks are rinsed with water, washed with a standard shampoo and then dried.

This gives in both cases a coppery shade, with a good quality of the fibre.

Example 7

This example illustrates a composition comprising ascorbic acid.

The composition below is prepared:

| | |
|---|---|
| lauric acid monoisopropanolamide | 3 |
| ethoxylated lauryl alcohol (12 EO) | 7 |
| ethoxylated oleocetyl alcohol (30 EO) | 4 |
| ethoxylated decyl alcohol (3 EO) | 10 |
| cetylstearyl alcohol (C16-C18 - 50/50) | 11.5 |
| diethylene triamine pentacetic acid, pentasodium salt, in aqueous solution at 40% | 4 |
| kaolin | 1.2 |
| 1,3-diaminopropane | 0.4 |
| Polyquaternium 6 | 4 |
| propylene glycol | 7 |
| Carbopol ETD 2020 | 0.6 |
| ammonium chloride | 3.78 |
| titanium oxide | 0.15 |
| sequestrants | 0.25 |

-continued

| | |
|---|---|
| ascorbic acid | 0.25 |
| reducing agents | q.s |
| fragrance | 0.6 |
| aqueous ammonia (containing 20.5% ammonia) | 6 |
| para-toluenediamine | 0.9 |
| 2,4-diaminophenoxyethanol HCl | 0.05 |
| 2-methylresorcinol | 0.6 |
| para-aminophenol | 0.8 |
| meta-aminophenol | 0.15 |
| resorcinol | 0.5 |
| 6-hydroxyindole | 0.15 |
| 2-methyl-5-hydroxyethylaminophenol | 0.3 |
| deionized water (qs) | qs 100 |

The composition is then mixed with a 30-volume oxidizing composition (dilution 1 to 1 by weight).

The resulting mixture is applied to locks of natural hair containing 90% of white hairs.

The mixture is left to take for 10 minutes at ambient temperature (23° C.+/−3° C.).

At the end of this application time, the locks are rinsed with water, washed with a standard shampoo and then dried.

This gives a coppery shade with a good quality of the fibre.

Example 8

This example illustrates a composition comprising a fatty acid.

The composition below is prepared:

| | |
|---|---|
| lauric acid | 3 |
| ethoxylated lauryl alcohol (12 EO) | 7 |
| ethoxylated oleocetyl alcohol (30 EO) | 4 |
| ethoxylated decyl alcohol (3 EO) | 10 |
| cetylstearyl alcohol (C16-C18 - 50/50) | 11.5 |
| diethylene triamine pentacetic acid, pentasodium salt, in aqueous solution at 40% | 4 |
| kaolin | 1.2 |
| 1,3-diaminopropane | 0.4 |
| Polyquaternium 6 | 4 |
| propylene glycol | 7 |
| Carbopol ETD 2020 | 0.6 |
| ammonium chloride | 3.78 |
| titanium oxide | 0.15 |
| sequestrants | qs |
| reducing agents | qs |
| antioxidants | qs |
| fragrance | 0.6 |
| aqueous ammonia (containing 20.5% ammonia) | 6 |
| para-toluenediamine | 1.23 |
| 2,4-diaminophenoxyethanol HCl | 0.04 |
| para-aminophenol | 0.67 |
| 2-amino-2-hydroxytoluene | 0.21 |
| meta-aminophenol | 0.6 |
| resorcinol | 0.84 |
| 6-hydroxyindole | 0.08 |
| deionized water (qs) | 100 |

The composition is then mixed with a 30-volume oxidizing composition (dilution 1 to 1 by weight).

The resulting mixture is applied to locks of natural hair containing 90% of white hairs.

The mixture is left to take for 10 minutes at ambient temperature (23° C.+/−3° C.).

At the end of this application time, the locks are rinsed with water, washed with a standard shampoo and then dried.

This gives a mahogany shade with a good quality of the fibre.

Example 9

This example illustrates the influence of the presence of a cationic polymer on the dyeing properties of the resulting composition.

The compositions below are prepared (amounts given in g % of active substance):

| | Composition A inventive | Composition B comparative |
|---|---|---|
| ethoxylated lauryl alcohol (12 EO) | 7.0 | 7.0 |
| ethoxylated oleocetyl alcohol (30 EO) | 4.0 | 4.0 |
| ethoxylated decyl alcohol (3 EO) | 10 | 10 |
| cetylstearyl alcohol (C16-C18 - 50/50) | 11.5 | 11.5 |
| tetramethylhexamethylenediamine/ 1,3-dichloropropylene polycondensate in aqueous solution | 2.4 | — |
| propylene glycol | 7.0 | 7.0 |
| ammonium chloride | 3.78 | 3.78 |
| titanium oxide | 0.15 | 0.15 |
| glycol distearate | 2.0 | 2.0 |
| reducing agent | qs | qs |
| sequestrant | qs | qs |
| fragrance | qs | qs |
| deionized water (QS) | QS 100 | QS 100 |
| aqueous ammonia (containing 20.5% ammonia) | 6 | 6 |
| toluene-2,5-diamine | 0.37 | 0.37 |
| 1-methyl-2-hydroxy-4-aminobenzene | 0.82 | 0.82 |
| para-aminophenol | 0.47 | 0.47 |
| 1,3-dihydroxybenzene (resorcinol) | 0.01 | 0.01 |
| 1-methyl-2-hydroxy-4-beta-hydroxyethylaminobenzene | 0.615 | 0.615 |

Each composition is mixed with a 30-volume oxidizing agent (dilution 1 to 1 by weight).

Each of the resulting mixtures is applied to locks of hair of average sensitivity (alkaline solubility 20%).

The locks thus treated are left to take for 10 minutes at ambient temperature (23° C.+/−3° C.).

At the end of this application time, the locks are rinsed with water, washed with a standard shampoo and then dried.

24 hours after colouring, calorimetric measurements are made using a Minolta CM-2600D calorimeter, in the Lab system.

The power and the rise between compositions A and B are measured:

The power is evaluated by the value of L*.

The lower L* is, the more powerful is the colouring obtained.

The rise corresponds to the difference in colour between the uncoloured lock and the coloured lock.

It is calculated according to the following equation:

$$DE=[(L^*-L^*_0)^2+(a^*+a^*_0)^2+(b^*-b^*_0)^2]^{1/2}$$

in which $L^*$, $a^*$ and $b^*$ are the coefficients relating to the coloured lock and $L^*_0$, $a^*_0$ and $b^*_0$ are the coefficients relating to the uncoloured lock.

The higher DE is, the greater is the rise in colour.

| Results | | |
|---|---|---|
| Composition | L* | DE |
| Uncoloured lock | 59.78 | — |
| Composition A, according to the invention | 22.64 | 43.76 |
| Composition B, comparative | 26.05 | 40.24 |

From these results it is observed that the composition according to the invention allows colorations to be obtained which are more powerful and exhibit a greater rise than those obtained by employing comparative compositions that do not include a cationic polymer.

The invention claimed is:

1. A composition for coloring keratin fibers, comprising, in a cosmetically acceptable medium, at least one oxidation dye, aqueous ammonia, ammonium chloride in an amount greater than 1.5% by weight relative to the total weight of the composition, and at least one additive selected from ceramides, silicas, crosslinked homopolymers of acrylic acid, copolymers of dialkyldiallylammonium chloride and acrylic acid, and cationic polymers composed of repeat units of formula A below:

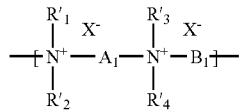

in which:
(i) $R'_1$, $R'_2$, $R'_3$ and $R'_4$, which are identical or different, are chosen from aliphatic, alicyclic, and aryl aliphatic groups containing 1 to 6 carbon atoms, and aliphatic hydroxyl ($C_1$-$C_6$) alkyl groups; or
(ii) $R'_1$, $R'_2$, $R'_3$ and $R'_4$, together or separately, constitute, with the nitrogen atoms to which they are attached, saturated heterocycles having five or six members, optionally comprising a second heteroatom other than nitrogen; or
(iii) $R'_1$, $R'_2$, $R'_3$ and $R'_4$ are chosen from linear and branched $C_1$-$C_6$ alkyl groups substituted by a nitrile, ester, acyl, amide; —CO—O—$R'_5$-D groups; and —CO—NH—$R'_5$-D groups, in which $R'_5$ is a $C_1$-$C_6$ alkylene group and D is a quaternary ammonium group containing $C_1$-$C_6$ alkyl groups which are identical or different;
$A_1$ and $B_1$ are chosen from polymethylene groups containing 2 to 6 carbon atoms, which may be linear or branched, saturated or unsaturated, and may contain bonded to (substitutent) or intercalated in the main chain, a $C_6$ aromatic ring, or an oxygen or sulphur atom, or sulphoxide, sulphone, disulphide, amino, alkylamino, hydroxyl, quaternary ammonium, ureido or ester groups or combinations thereof; and
$X^-$ is an anion derived from an organic or inorganic acid; and in which:
$A_1$, $R'_1$ and $R'_3$ may form, with the two nitrogen atoms to which they are attached, a piperazine ring.

2. The composition according to claim 1, wherein the ammonium chloride is present in an amount greater than or equal to 3% by weight relative to the total weight of the composition.

3. The composition according to claim 1, wherein the aqueous ammonia, expressed in terms of gaseous ammonia, is present in an amount greater than or equal to 0.5% by weight relative to the weight of the total composition.

4. The composition according to claim 3, wherein the weight ratio of the amount of ammonium chloride to the amount of aqueous ammonia (expressed in terms of gaseous ammonia) has a value of greater than or equal to 2.

5. The composition according claim 1, wherein the at least one additive is present in an amount, for each additive, ranging from 0.001% to 10% by weight relative to the total weight of the composition.

6. The composition according to claim 1 further comprising at least one oxidizing agent.

7. The composition according to claim 6, wherein the at least one oxidizing agent is hydrogen peroxide.

8. A method for coloring human keratin fibers, comprising applying to the human keratin fibers at least one coloring composition in the presence of at least one composition comprising at least one oxidizing agent, and leaving the composition on the keratin fibers for an application time of less than or equal to 20 minutes,
wherein the coloring composition comprises at least one oxidation dye, aqueous ammonia, ammonium chloride in an amount greater than 1.5% by weight relative to the total weight of the composition, and at least one additive selected from ceramides, silicas, crosslinked homopolymers of acrylic acid, copolymers of dialkyldiallylammonium chloride and acrylic acid, and cationic polymers composed of repeat units of formula A below:

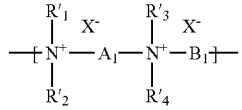

in which:
(i) $R'_1$, $R'_2$, $R'_3$ and $R'_4$, which are identical or different, are chosen from aliphatic, alicyclic, and aryl aliphatic groups containing 1 to 6 carbon atoms, and aliphatic hydroxyl ($C_1$-$C_6$) alkyl groups; or
(ii) $R'_1$, $R'_2$, $R'_3$ and $R'_4$, together or separately, constitute, with the nitrogen atoms to which they are attached, saturated heterocycles having five or six members, optionally comprising a second heteroatom other than nitrogen; or
(iii) $R'_1$, $R'_2$, $R'_3$ and $R'_4$ are chosen from linear and branched $C_1$-$C_6$ alkyl groups substituted by a nitrile, ester, acyl, amide; —CO—O—$R'_5$-D groups; and —CO—NH—$R'_5$-D groups, in which $R'_5$ is a $C_1$-$C_6$ alkylene group and D is a quaternary ammonium group containing $C_1$-$C_6$ alkyl groups which are identical or different;
$A_1$ and $B_1$ are chosen from polymethylene groups containing 2 to 6 carbon atoms, which may be linear or branched, saturated or unsaturated, and may contain bonded to (substitutent) or intercalated in the main chain, a $C_6$ aromatic ring, or an oxygen or sulphur atom, or sulphoxide, sulphone, disulphide, amino, alkylamino, hydroxyl, quaternary ammonium, ureido or ester groups or combinations thereof; and
$X^-$ is an anion derived from an organic or inorganic acid; and in which:
$A_1$, $R'_1$ and $R'_3$ may form, with the two nitrogen atoms to which they are attached, a piperazine ring.

9. The method according to claim 8, comprising applying the at least one coloring composition and the at least one composition comprising at least one oxidizing agent to the human keratin fibers in any order, and without rinsing the human keratin fibers in between the applications.

10. The method according to claim 8, comprising applying at least one ready-to-use composition to the keratin fibers, wherein the at least one ready-to-use composition is created, at or close to the time of application, by combining the at least one coloring composition and the at least one composition comprising at least one oxidizing agent.

11. A multiple-compartment device comprising
at least one first compartment containing at least one coloring composition; and at least one second compartment containing a composition comprising at least one oxidizing agent,
wherein the at least one coloring composition of comprises at least one oxidation dye, aqueous ammonia, ammonium chloride in an amount greater than 1.5% by weight relative to the total weight of the composition, and at least one additive selected from ceramides, silicas, crosslinked homopolymers of acrylic acid, copolymers of dialkyldiallylammonium chloride and acrylic acid, and cationic polymers composed of repeat units of formula A below:

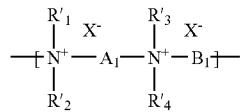

in which:
(i) $R'_1$, $R'_2$, $R'_3$ and $R'_4$, which are identical or different, are chosen from aliphatic, alicyclic, and aryl aliphatic groups containing 1 to 6 carbon atoms, and aliphatic hydroxyl ($C_1$-$C_6$) alkyl groups; or
(ii) $R'_1$, $R'_2$, $R'_3$ and $R'_4$, together or separately, constitute, with the nitrogen atoms to which they are attached, saturated heterocycles having five or six members, optionally comprising a second heteroatom other than nitrogen; or
(iii) $R'_1$, $R'_2$, $R'_3$ and $R'_4$ are chosen from linear and branched $C_1$-$C_6$ alkyl groups substituted by a nitrile, ester, acyl, amide; —CO—O—$R'_5$-D groups; and —CO—NH—$R'_5$-D groups, in which $R'_5$ is a $C_1$-$C_6$ alkylene group and D is a quaternary ammonium group containing $C_1$-$C_6$ alkyl groups which are identical or different;
$A_1$ and $B_1$ are chosen from polymethylene groups containing 2 to 6 carbon atoms, which may be linear or branched, saturated or unsaturated, and may contain bonded to (substitutent) or intercalated in the main chain, a $C_6$ aromatic ring, or an oxygen or sulphur atom, or sulphoxide, sulphone, disulphide, amino, alkylamino, hydroxyl, quaternary ammonium, ureido or ester groups or combinations thereof; and
$X^-$ is an anion derived from an organic or inorganic acid; and in which:
$A_1$, $R'_1$ and $R'_3$ may form, with the two nitrogen atoms to which they are attached, a piperazine ring.

* * * * *